United States Patent
Vivas-Mejia et al.

(10) Patent No.: US 9,895,312 B2
(45) Date of Patent: Feb. 20, 2018

(54) NANOLIPOSOMAL C-MYC-SIRNA INHIBITS IN VIVO TUMOR GROWTH OF CISPLATIN-RESISTANT OVARIAN CANCER

(71) Applicants: Pablo E. Vivas-Mejia, San Juan, PR (US); Jeyshka M. Reyes Gonzalez, San Juan, PR (US); Anil K. Sood, Houston, TX (US)

(72) Inventors: Pablo E. Vivas-Mejia, San Juan, PR (US); Jeyshka M. Reyes Gonzalez, San Juan, PR (US); Anil K. Sood, Houston, TX (US)

( * ) Notice: Subject to any disclaimer, the term of this patent is extended or adjusted under 35 U.S.C. 154(b) by 38 days.

(21) Appl. No.: 14/681,875

(22) Filed: Apr. 8, 2015

(65) Prior Publication Data
US 2015/0306036 A1   Oct. 29, 2015

Related U.S. Application Data

(60) Provisional application No. 61/976,973, filed on Apr. 8, 2014.

(51) Int. Cl.
| | |
|---|---|
| *C12N 15/113* | (2010.01) |
| *A61K 9/127* | (2006.01) |
| *A61K 31/7088* | (2006.01) |
| *A61K 33/24* | (2006.01) |
| *A61K 45/06* | (2006.01) |
| *A61K 31/713* | (2006.01) |
| *C12N 15/11* | (2006.01) |
| *A61K 9/00* | (2006.01) |

(52) U.S. Cl.
CPC ........ *A61K 9/1272* (2013.01); *A61K 9/0019* (2013.01); *A61K 9/1271* (2013.01); *A61K 31/7088* (2013.01); *A61K 31/713* (2013.01); *A61K 33/24* (2013.01); *A61K 45/06* (2013.01); *C12N 15/11* (2013.01); *C12N 2320/31* (2013.01); *C12N 2320/32* (2013.01)

(58) Field of Classification Search
USPC .................. 536/23.1, 24.5; 424/450; 514/44
See application file for complete search history.

(56) References Cited

PUBLICATIONS

Li et al. J. Control Release Feb. 28, 2012 vol. 158(1):108-114.*
Weiss et al. Journal of Investigative Dermatology, 2010 vol. 130:2699-2701.*

* cited by examiner

*Primary Examiner* — Terra C Gibbs
(74) *Attorney, Agent, or Firm* — Eugenio J. Torres Oyola; Victor Rodriguez Reyes; Ferraiuoli LLC

(57) ABSTRACT

The present invention discloses c-MYC-siRNA formulation as a potential therapeutic target for cisplatin-resistant ovarian cancer. It is disclosed targeting c-MYC with small interfering RNA (siRNA) in the cisplatin-resistant ovarian cancer cell line inducing a significant cell growth arrest and inhibition of cell proliferation. Apoptosis and arrest of cell cycle progression were also observed after c-MYC-siRNA-based silencing of c-MYC. Furthermore, delivering nanoliposomal c-MYC-siRNA, decreased tumor weight and number of tumor nodules compared with a liposomal-negative control siRNA.

2 Claims, 18 Drawing Sheets

|  | 1 | 2 | 3 | 4 |
|---|---|---|---|---|
| siRNA | 5.0 | 5.0 | 5.0 | 5.0 |
| DOPC | + | + | + | + |
| Cholesterol | 1.0 | 1.0 | - | - |
| Tween-20 | - | - | 2.75 | 2.75 |
| PEG-2000 | 1.76 | 0.7 | 1.76 | 0.7 |
| t-butanol | 200ul | 200ul | 200ul | 200ul |
| SIZE | 187.6 ± 23.5 | 176.9 ± 12.1 | 232.7 ± 12.1 | 224.4 ± 31.8 |

| Formulation | Mean Particle Size (nm) | Mean Z Potential (mV) | Encapsulation Efficiency (%) |
|---|---|---|---|
| 25% Cholesterol | 93.0 | -2.50 | 74.3 |
| 50% Cholesterol | 116.2 | -2.81 | 75.5 |
| 75% Cholesterol | 226.3 | -2.15 | N/A* |

Fig. 6

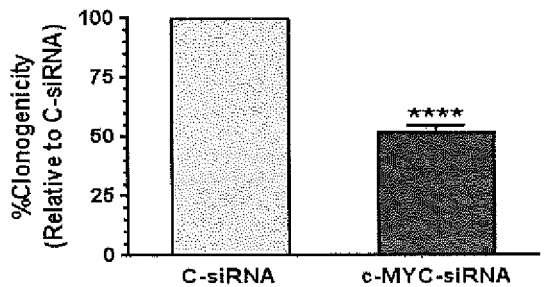
Fig. 12
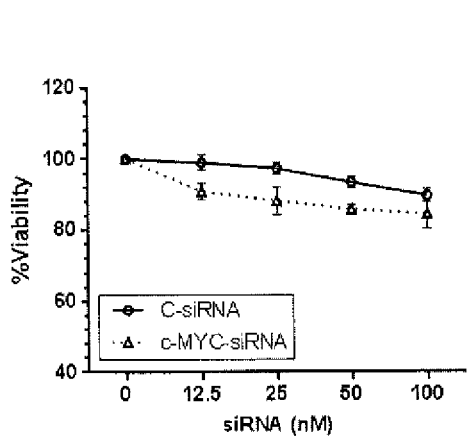 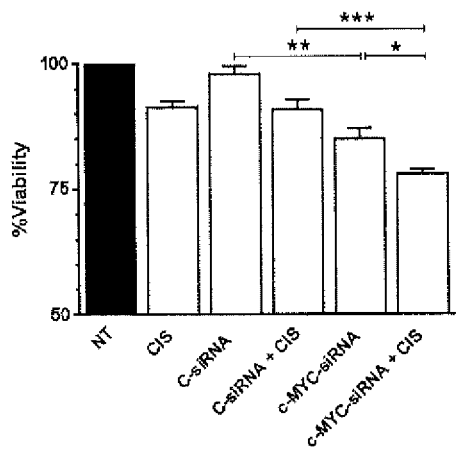
Fig. 13                Fig. 14

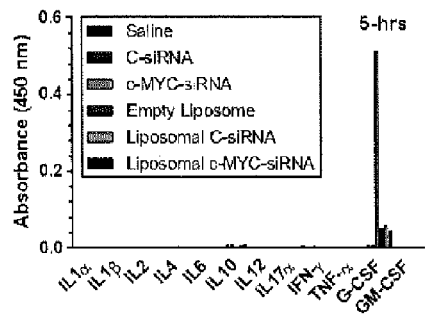 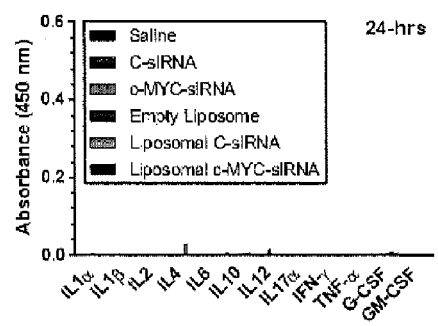
Fig. 21A                Fig. 21B
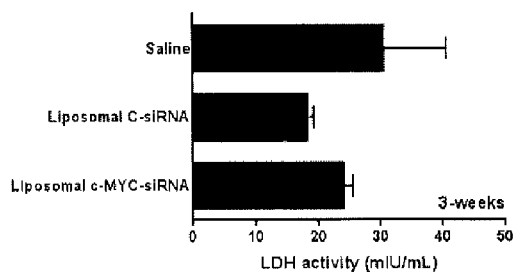 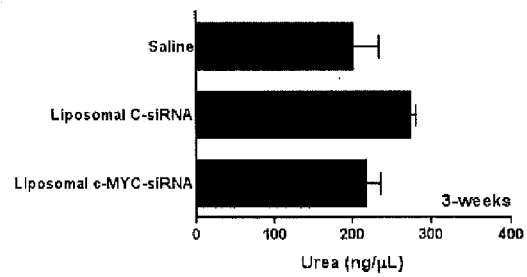
Fig. 21C                Fig. 21D
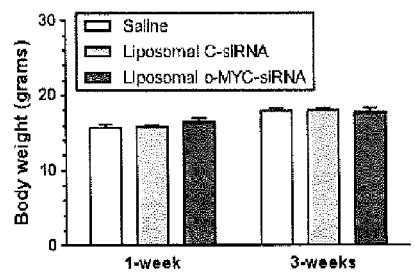
Fig. 21E

| Time (min) | Mean Particle Size (nm) | Mean Z Potential (mV) |
|---|---|---|
| 0 | 143.5 | -2.40 |
| 30 | 150.8 | -2.05 |
| 60 | 134.9 | -2.00 |
| 120 | 139.5 | -1.46 |

Figure 22

| Time (weeks) | Mean Particle Size (nm) | Mean Z Potential (mV) |
|---|---|---|
| 0 | 111.5 | -2.24 |
| 2 | 105.6 | -2.05 |
| 4 | 121.3 | -2.75 |

Fig. 23

NANOLIPOSOMAL C-MYC-SIRNA INHIBITS IN VIVO TUMOR GROWTH OF CISPLATIN-RESISTANT OVARIAN CANCER

STATEMENT REGARDING FEDERALLY SPONSORED RESEARCH AND DEVELOPMENT

This project is supported in part by the National Institutes of Health (NIH) 1K22CA166226-01A1 (PEVM), R25GM061838 (MGRS-RISE Program), G12MD007600 (NIMHD) and the UPR-MDACC Partnership in Cancer Research Training Program.

RELATED APPLICATIONS

N/A

BACKGROUND OF THE INVENTION

Discussion of the Background

Ovarian cancer presents non-specific symptoms and it has the highest mortality of all gynecological cancers. About 21,980 new ovarian cancer cases and 14,270 deaths are expected in the United States in 2014.

Surgery and platinum-based adjuvant chemotherapy, such as cisplatin (CIS), are the most common treatments for ovarian cancer. Unfortunately, over 70% of women develop chemoresistance. The exact mechanism of CIS resistance is not known, however, evidence indicates that activation of the oncogenic transcription factor c-MYC is involved in drug resistance. Our previous findings indicate that cisplatin-resistant ovarian cancer cells express higher c-MYC protein levels when compared to their sensitive counterparts.

Small modified single-stranded RNAs have emerged as a treatment modality of exceptional promise for cancer treatment among the drugs that are currently under clinical trial. The mechanism by which these small RNA molecules act are normally know as interference RNA (siRNA). Basically, small RNAs bind to messenger RNA (mRNA) and block protein synthesis. Systemic administration of these small RNA (siRNA) molecules has remained a major challenge due to its short half-life, lack of ability to penetrate the plasma membrane, and potential toxicity (including activation of the immune response). Nanoliposome-based delivery systems have been proposed to address these concerns. Therefore, development of safe, easy to administer, and efficient delivery systems that achieve prolonged effect is of substantial clinical importance. Further there is a need of the incorporation of polyethylene glycol (PEG) on the surface of the liposomal carrier to extend blood-circulation time. Thus, a liposomal formulation containing folate on its surface will increase the stability in the circulation.

The c-myc (v-myc avian myelocytomatosis viral oncogene homolog) binds to specific DNA sequences to activate gene expression. c-MYC regulates the expression of genes involved in a myriad of cellular processes including replication, growth, metabolism, differentiation, and apoptosis. Overexpression of c-MYC has been reported in most, if not all, types of human malignancies. c-MYC coordinates the activation and repression of protein-coding genes involved in cell growth, proliferation, loss of differentiation and apoptosis; and noncoding RNAs such as microRNAs (miR-NAs).

Moreover, c-MYC is commonly dysregulated in cancer, reprogramming gene expression to facilitate cellular proliferation and tumorigenesis. In fact, the c-MYC gene is amplified in 30-60% of human ovarian cancers. Given the pivotal role of c-MYC in ovarian cancer, its therapeutic targeting in chemoresistance is important.

In conclusion, ovarian cancer is the deadliest of gynecological cancers in the United States. With fewer than 15% of cases diagnosed early, ovarian cancer continues to be characterized by late-stage presentation. Treatment for ovarian cancer usually involves surgical cytoreduction followed by platinum-based chemotherapy. Unfortunately, despite initial, more than 70% of ovarian cancer patients develop cisplatin resistance, relapse and therapeutic failure. Therefore, there is a need of novel therapies focused on targets within cancer cell survival pathways for advanced stage drug resistant such as ovarian cancer.

SUMMARY OF THE INVENTION

The small interference RNA (siRNA) is a new therapeutic modality to target specific genes increased in cancer cells. siRNA are 22-base ribonucleic acid (RNA) molecules that bind to a specific region in the target gene and avoid the protein synthesis inside cell. One of the major changes of the siRNA-based therapy is that the half-life of siRNA molecules is very short (minutes to hours). Thus, a carrier is necessary to encapsulate siRNA molecules and avoid their degradation in the blood. Several carries have been proposed. However, liposomes are the most common drug carriers.

The major advantages of liposomes are that they are biodegradable and biocompatible. When the size of liposomes is in the nanometer (nm) scale (1 nm is one-billionth of a meter), they are called nanoliposomes.

c-MYC is a protein highly abundant in several types of cancers. C-MYC is considered as an oncogene because it induces malignant transformation. We found that c-MYC is overexpressed in ovarian cancer cells that are resistant to chemotherapy. In addition, we use an internet searchable database (The Cancer Genome Atlas) and found that the life expectancy of ovarian cancer patients with high c-MYC levels is lower compared with ovarian cancer patients with small c-MYC levels.

Thus, we designed a nanoliposomal formulation to encapsulate c-MYC-siRNA with therapeutic purposes.

One object of the present disclosure is to overcome the limitations of the previous therapies. In accordance with an exemplary embodiment the nanoliposomal formulation comprises at least a lipid, and c-MYC-siRNA, each in a ratio of 1 μg c-MYC-siRNA:10 μg DOPC (1,2-Dioleoyl-sn-glycero-3-phosphocholine), cholesterol 40% (w/w) DOPC, 10% PEG-2000 (mol/mol) of DOPC.

Another object is to disclose a nanoliposomal formulation to encapsulate c-MYC-siRNA with therapeutic purposes.

Another object is to assess the molecular and therapeutic effects of small-interference RNA (siRNA)-mediating c-MYC targeting in cisplatin-resistant ovarian cancer.

Importantly, targeting c-MYC with small interfering RNA (siRNA) in the cisplatin-resistant ovarian cancer cell line, A2780CP20, induced a significant cell growth arrest and inhibition of cell proliferation. This effect was corroborated in another two ovarian cancer cell lines (A2780CIS and HEYA8 ovarian cancer cells). Apoptosis and arrest of cell cycle progression were also observed after siRNA-based silencing of c-MYC. These results were confirmed by Western blot analysis. Furthermore, in vivo delivery of c-MYC-siRNA in a murine xenograft model of cisplatin-resistant ovarian cancer was achieved by using DOPC/PEG-2000- based nanoliposomes. A single weekly injection of nanoliposomal c-MYC-siRNA, during a four week period, decreased tumor weight and number of tumor nodules compared with a liposomal-negative control siRNA. Finally, Liposomal c-MYC-siRNA did not induced toxic or immune effects in mice. These data advance c-MYC-siRNA as a therapeutic target for cisplatin-resistant ovarian cancer.

Different aspects of the invention, their configuration, and mode of operation will be best understood, and additional objects and advantages thereof will become apparent, by the following detailed description of a preferred embodiment taken in conjunction with the accompanying drawings.

The Applicant hereby asserts, that the disclosure of the present application may include more than one invention, and, in the event that there is more than one invention, that these inventions may be patentable and non-obvious one with respect to the other.

Further, the purpose of the accompanying abstract is to enable the U.S. Patent and Trademark Office and the public generally, and especially the scientists, engineers, and practitioners in the art who are not familiar with patent or legal terms or phraseology, to determine quickly from a cursory inspection the nature and essence of the technical disclosure of the application. The abstract is neither intended to define the invention of the application, which is measured by the claims, nor is it intended to be limiting as to the scope of the invention in any way.

BRIEF DESCRIPTION OF THE DRAWINGS

The accompanying drawings, which are incorporated herein, constitute part of the specifications and illustrate the preferred embodiment of the invention.

FIG. 6 is a table summarizing the size, charge and encapsulation efficiency of liposomes with different cholesterol ratios FIG. 7 graph shows the cell toxicity results.

FIG. 12 shows the reduction in colony formation after c-MYC-siRNA-based silencing of c-MYC in A2780CIS cells.

FIG. 13 Shows that in A2780 cells (very low c-MYC expression) the c-MYC siRNA does not induce any toxic effect.

FIG. 14 shows that combination of c-MYC siRNA plus Cisplatin (CIS) further reduce tumor growth of A2780CP20 cells.

c-MYC-siRNA.

Figure 17:
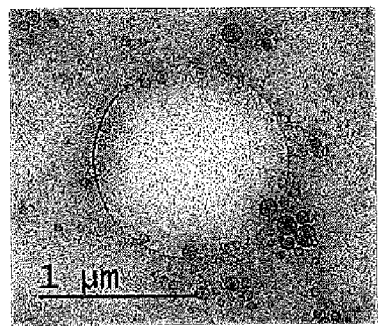

FIG. 17 shows a cryo Electron micrographs indicating that the nanoliposmal formulation are small unilamelar vesicles.

Figure 18A:
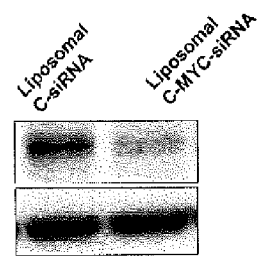
Figure 18B:
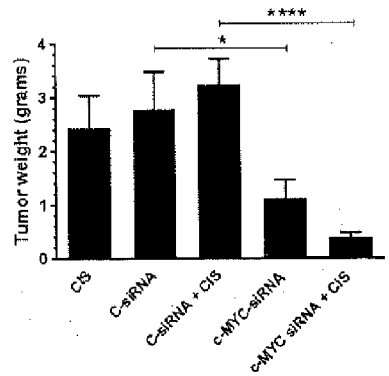
Figure 18C:
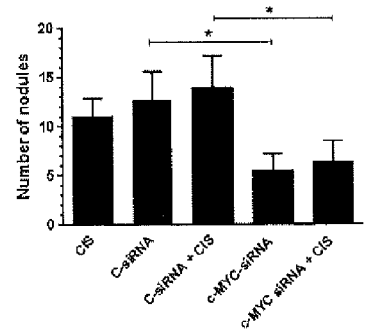

FIG. 18A-18C shows the in vivo therapeutic efficacy of liposomal c-MYC siRNA.

FIG. 19A-19D shows the effect of c-MYC-siRNA-mediated c-MYC silencing in HEYA8 ovarian cancer cells.

FIG. 20A-20D shows in vitro and in vivo characterization of liposomal formulations.

FIG. 21A-21E shows immunostimulatory effects and safety of DOPC-PEG-c-MYC-siRNA.

FIG. 22 is a table showing the stability at room temperature of liposomal after reconstitution.

FIG. 23 is a table showing the stability of the liposomal formulation stored at 4° C. without reconstitution.

DESCRIPTION OF THE PREFERRED EMBODIMENT

Figure 1:
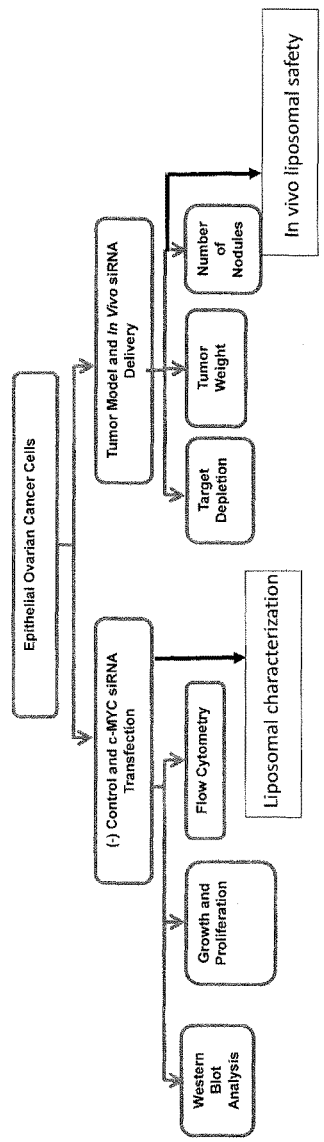
FIG. 1 Schematic diagram of experiments.
Figure 2:
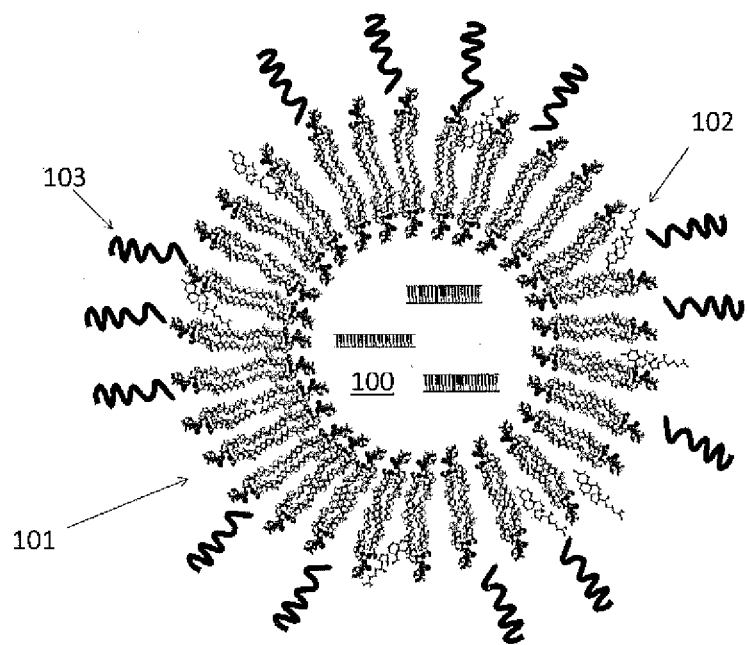
FIG. 2 shows a schematic representation of a PEG-2000 nanoliposome.

FIG. 1. Schematic diagram of experiments performed for the fully liposomal characterization and uses. A schematic representation of the nanoliposomes is shown in FIG. 2. The nanoliposomal formulation presented comprises lipids and c-MYC-siRNA with a preferred ratio, for example:

1 μg c-MYC-siRNA 100:10 μg DOPC 101, cholesterol 40% 102 (w/w) DOPC, 10% PEG-2000 103 (mol/mol) of DOPC.

FIG. 2 is a representation of the nanoliposomes. Specific amounts of these components are mixed in excess of ter-butanol as the dissolvent. The mixture is frozen at −80° C. or lower. Then, tubes are lyophilized to evaporate the dissolvent (ter-butanol). The lyophilized power is dissolved in DPBS. For liposomal characterization and for mice injections liposomes are vortexed (2-5 minutes) or sonicated (10 min).

Methods

Nanoliposomal Characterization

Four c-MYC-siRNA-contained nanoliposomes formulations were prepared as described above. Then, liposomes were resuspended in DPBS. The particle size and charge were measured in a ZetaPals instrument.

Nanoliposome Size.

nanoliposomes (containing 5 μg of c-MYC-siRNA) were resuspended in 2 ml DPBS. 1.5 ml was put in a cuvette. The cuvette was put in the ZetaPals instrument for size measurements.

Nanoliposome Charge.

Nanoliposmes (containing 5 μg of c-MYC-siRNA) were resuspended in 2 ml DPBS. Fifty μL of this solution was mixed with 2 mL of DPBS 0.01×. The final mixture was put in a cuvette, and the cuvette loaded on the Zeta Potential Analyzer machine.

Encapsulation Efficiency.

1. 20 μg c-MYC-siRNA-containing liposomes were dissolved in 400 μL of DPBS. Four-hundred μL of the mixture was loaded in a centrifugal filter F of 50 kDa (Millipore). The filter F was centrifuged at 7,500 rpm for 10 min. 10 μL of the liquid on the bottom of the tube T was used to calculate the c-MYC-siRNA concentration with the Nano-Drop-1000 instrument. Naked c-MYC-siRNA dissolved in DPBS (no liposomes) was used as a control. Because the naked c-MYC-siRNA is completely dissolved all amount should go through the filter F after centrifugation. 400 μL of tritox X-100 (0.5%) was added in the top of the filter and the tube (containing the filter) was centrifuged again.

The encapsulation efficiency was calculated with the following equation:

$$\% E = (\text{total siRNA} - \text{free siRNA}/\text{total siRNA}) \times 100$$

Figure 3:
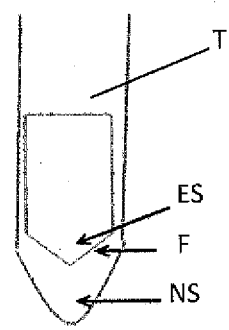
FIG. 3 shows a Liposomal c-MYC-siRNA solution loaded in the filter.

As shown in FIG. 3 the Liposomal c-MYC-siRNA solution is loaded in the tube. The tube is centrifuged. The non-encapsulated NS c-MYC-siRNA cross the filter F. The encapsulated c-MYC-siRNA ES remains in the filter F.

Liposomal Toxicity.

For toxicity; liposomal were prepared without c-MYC-siRNA. 50 µg of DOPC-containing nanoliposomes were dissolved in 2 ml of sterile DPBS. Serial dilutions of nanaliposomes were prepared in RPMI (10% fetal bovine serum) (see FIG. 4). One-hundred µl each dilution was added to the human ovarian cancer cell line, A2780CP20. Cells were incubated 72-hr with the liposomes. Then, the cell survival was calculated with the AlamarBlue dye (4). The percentage of survival was calculated relative to cells without any treatment.

The present disclosure includes in vitro and in vivo studies.

Nanoliposomal Size and Charge.

Figures 4, 5:
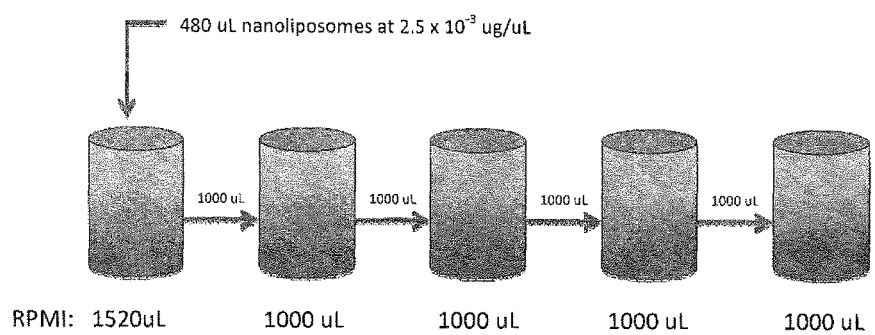
FIG. 4 shows a serial dilution of liposomal formulations.
FIG. 5 table contains the mean size of four c-MYC-siRNA-liposomal formulation tested.

The FIGS. 5 and 6 contains the mean size of four siRNA-liposomal formulation tested.

The following amount are in µl.

c-MYC-siRNA concentration stock=1 mg/ml

FIGS. 5 and 6 disclose several concentration combinations of the formulation in accordance with principles of the present disclosure. According to the results the selected liposomal formulation for in vitro and in vivo studies is the number 2 in FIG. 5 (table). 50 µg of DOPC liposomes were resuspended in 2 ml of DPBS for in vitro experiments.

Particle Charge and Encapsulation Efficiency

FIG. 6 shows a table summarizing the size, charge and encapsulation efficiency. The charge was measured for formulations 2 (see FIG. 5) at different cholesterol ratios. FIG. 6 indicate that the formulation containing 50% or 25% cholesterol are smaller in size and are the object of the present disclosure. The encapsulation efficiency shows that liposomal formulations containing 25% and 50% cholesterol were around the same. Thus, the formulation 2 was used for in vivo experimentation.

Toxicity.

Figure 7:
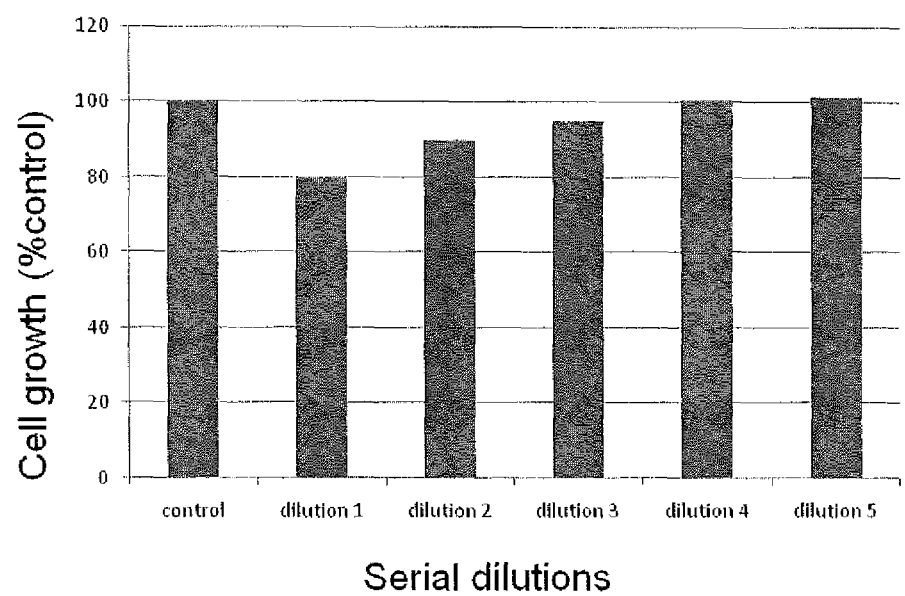
Figure 8A:
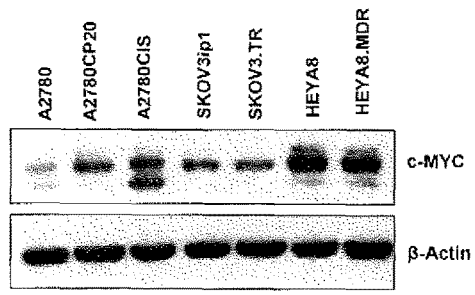
FIG. 8A-8B shows c-MYC expression levels in ovarian cancer cells.
Figure 8B:
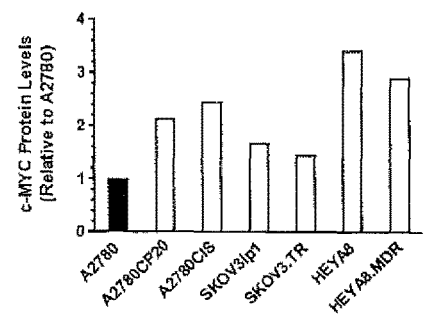
Figure 9A:
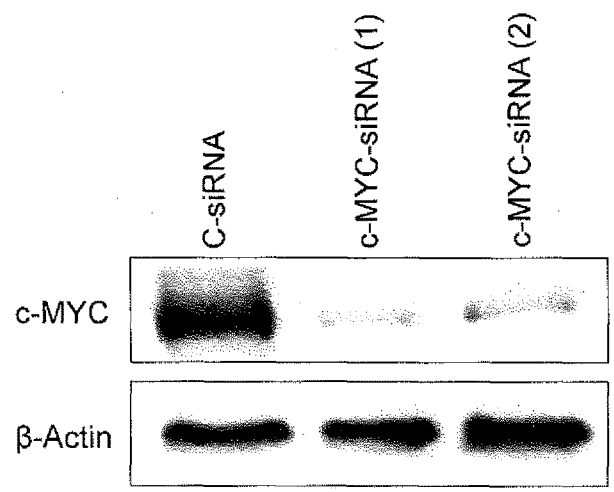
FIGS. 9A-9C shows the effective c-MYC silencing in vitro, and the effect of c-MYC-siRNA-mediated c-MYC silencing on colony formation and cell proliferation.
Figure 9B:
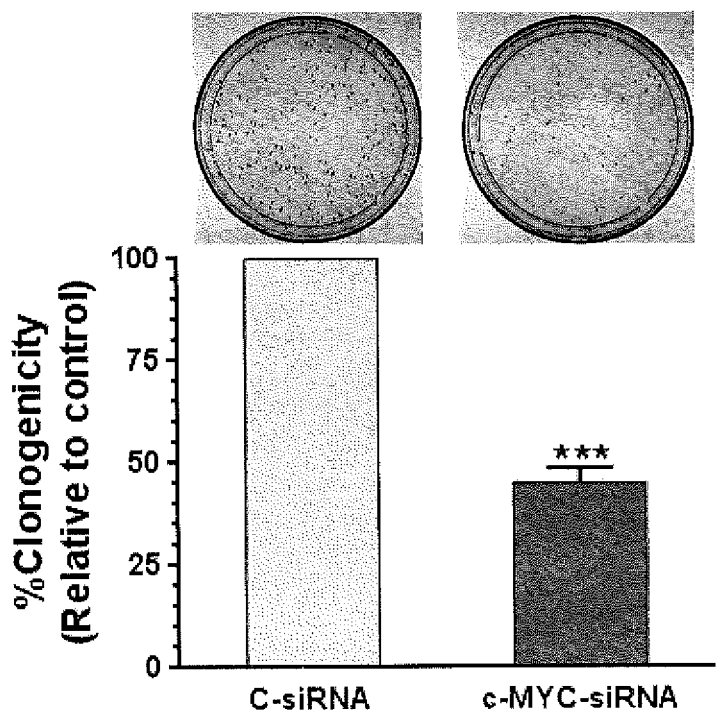
Figure 9C:
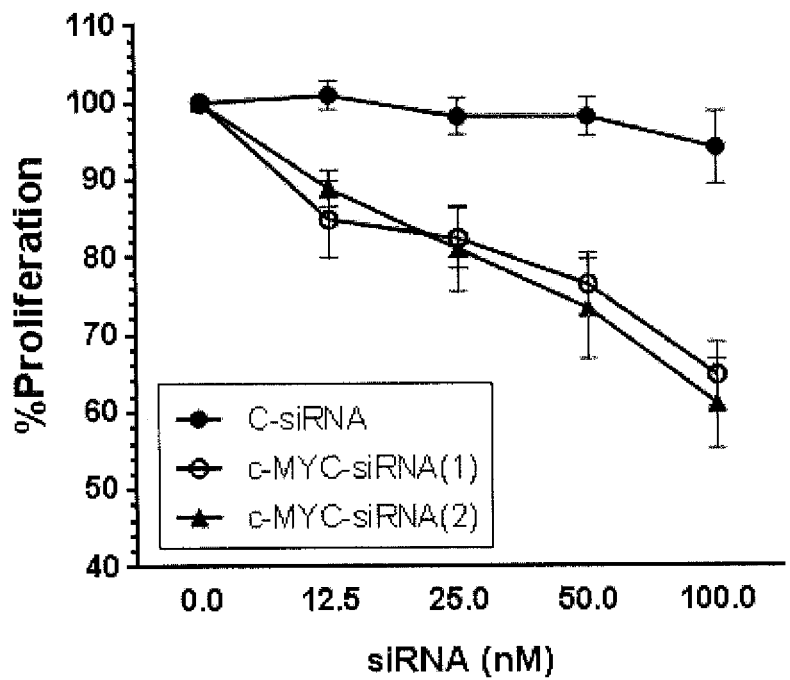

The graph, as shown in FIG. 7, shows that any of the dilutions of the formulation number 2 induced toxicity in the cells, which demonstrate the safety of this liposomal formulation obtained from the toxicity experiments. As shown in FIG. 7, regarding the cell toxicity results, the only dilution that reduced cell proliferation was the higher dilution. This reduced cell proliferation in 20%. However, this dilution contains much more liposomes that the ones injected in mice.

c-MYC expression levels in ovarian cancer cells is shown in FIG. 8. Ovarian cancer cell lines that are more resistant to chemotherapy express higher levels of c-MYC compared with cells that are more sensitive to chemotherapy. A densitometric analysis of the bands in the FIG. 8A confirmed these results (FIG. 8B). FIG. 9A-9C shows the effect of c-MYC-siRNA-mediated c-MYC silencing on colony formation and cell proliferation. As shown in FIG. 9A, A2780CP20 cells were transfected with 200 nM of two different c-MYC-siRNA targeting c-MYC reduced significantly the c-MYC levels compared with the control-siRNA or C-siRNA. As shown in FIG. 9B, colonies ≥50 were scored under a light microscope. The % of clonogenicity was calculated relative to C-siRNA (100 nM). The c-MYC-siRNA reduced in more than 50% the number of colonies compared with the control. As shown in FIG. 9C, A2780CP20 cells were transfected with a serial dilution of C-siRNA or c-MYC-targeted siRNAs. Cell proliferation was calculated spectrophotometrically using the Alamar blue dye. Averages±SEM are shown for at least three independent experiments. Significant difference at P<0.001 (***) is presented based on Student's t-test. C-MYC-siRNA reduced significantly the cell growth of cisplatin resistant cells.

Figure 10A:
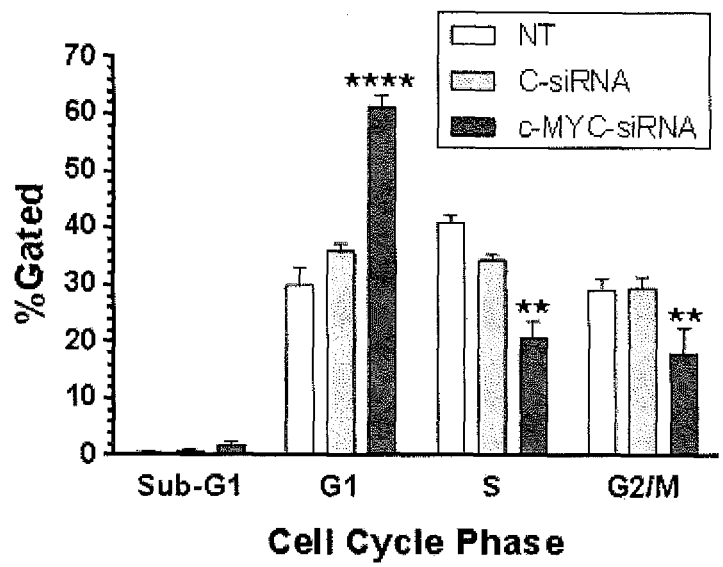
FIGS. 10A-10C shows effect of c-MYC-siRNA-mediated c-MYC silencing on cell cycle progression and apoptosis.
Figure 10B:
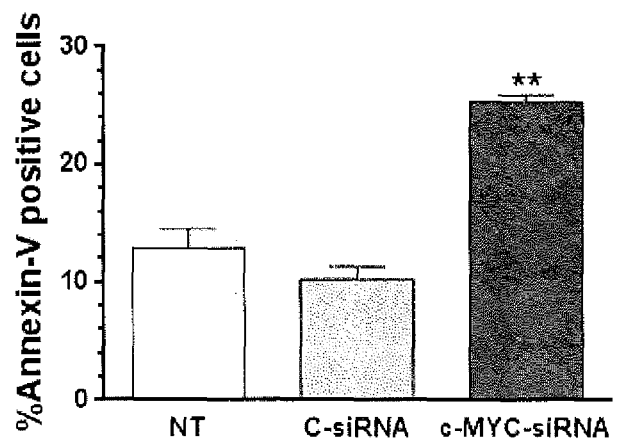
Figure 10C:
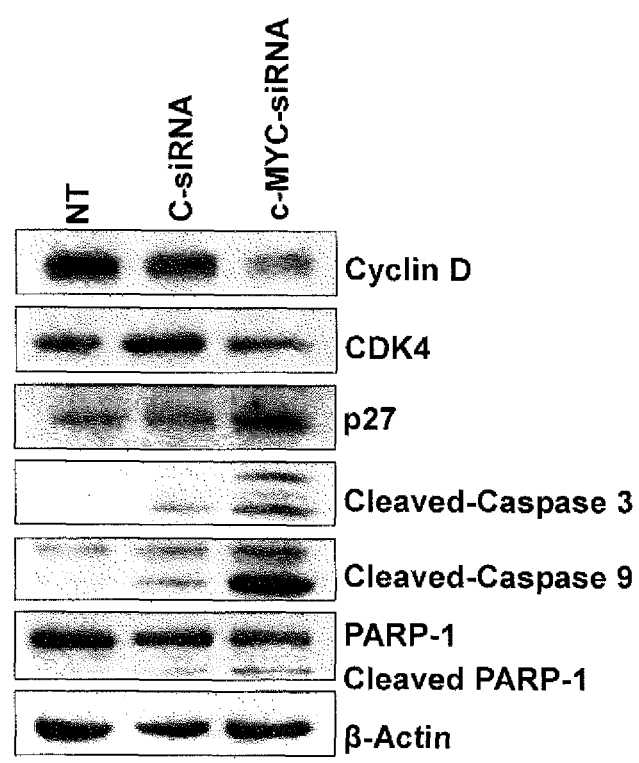

FIG. 10A-10C shows the effect of c-MYC-siRNA-mediated c-MYC silencing on cell cycle progression and apoptosis. A2780CP20 cells were transfected with 200 nM C-siRNA and c-MYC-targeted siRNA. As shown in FIG. 10A, cell cycle progression was evaluated using propidium iodide (PI) after forty-eight hours of c-MYC-siRNA transfection. As shown in FIG. 10B, apoptosis was evaluated using FITC-Annexin V/PI after seventy-two hours c-MYC-siRNA transfection. Averages±SEM are shown for at least two independent experiments. Significant difference, relative to C-siRNA, at P<0.01 () and P<0.0001 (**) are presented based on ANOVA and Student's t-test. The c-MYC-siRNA activated apoptosis in almost 30% compared with the control siRNA. FIG. 10C is representative Western blots show changes in the levels of key proteins involved in cell cycle progression and apoptosis following c-MYC-siRNA transfection.

Figure 15A:
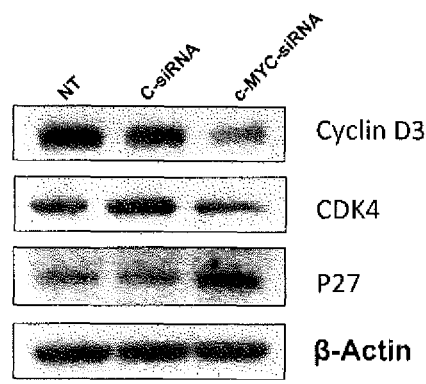
FIG. 15A-B shows the cell cycle progression proteins following c-MYC silencing.
Figure 15B:
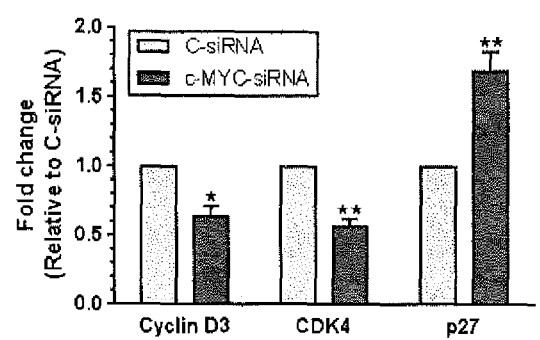
Figure 16A:
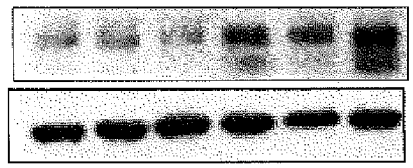
FIG. 16A-B shows in vitro effects of c-MYC overexpression.
Figure 16B:
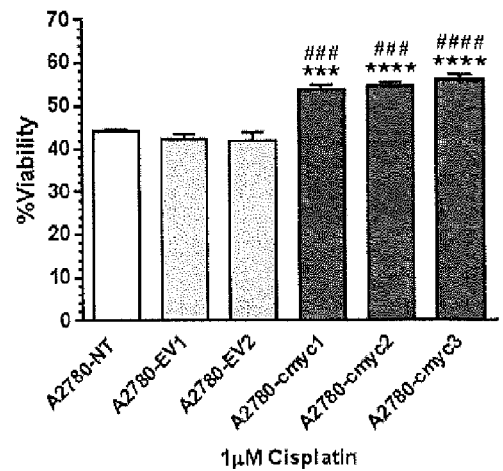

FIG. 11A-11D shows Kaplan-Meier survival curves indicating that ovarian cancer patient with higher c-MYC expression levels live less than patients with lower c-MYC expression levels. Transfection of c-MYC-siRNA also reduced the cell proliferation of another cisplatin (CIS) resistant ovarian cancer cells (A2780CIS) (FIG. 12). In addition, transfection of c-MYC siRNA in cells with very low c-MYC expression (A2780, FIG. 8A) did not induce cell toxicity (FIG. 13). Furthermore, the combination of c-MYC siRNA and cisplatin further potentiated the c-MYC siRNA effect (FIG. 14). Slicing of c-MYC also induced changes in proteins involved I cell cycle progression (FIG. 15A-15B).

c-MYC was overexpressed in cells with low c-MYC levels (A2780)(FIG. 16A). The rate of cell proliferation of these cells were higher compared with empty vectors (FIG. 16B). The effect of nanoliposomal-c-MYC-siRNA was tested on target depletion, and therapy efficacy. Nude mice were injected intraperitoneally (i.p.) with A2780CP20 cells. A nude mice-bearing tumors were injected i.p. with nanoliposomal siRNAs. Seven days post-injection, mice were sacrificed and the tumors were dissected. As shown is FIG. 18A, the anti-tumor effects of nanoliposomal-c-MYC-siRNA as compared to C-siRNA were tested in tumor-bearing mice. Tumor weight, as shown in FIG. 18B and number of nodules, as shown in FIG. 18C, were assessed in five treatment groups (10 mice each). All nanoliposomal-c-MYC-siRNAs and CIS treatments were injected i.p. once a week for 4 weeks. In vitro experiments were repeated in HEYA8 ovarian cancer cells which express high c-MYC levels (FIG. 19A-19D). Additional liposomal c-MYc-siRNA formulation was performed (FIG. 20A-20D) and FIGS. 22 and 23). The safety of nanoliposmes were tested in mice (FIG. 21A-21E).

Results

Western blot analysis was used to measure the c-MYC protein levels in a panel of ovarian cancer cells. Cisplatin-resistant cells expressed higher levels of c-MYC protein when compared to their sensitive counterparts.

c-MYC targeting by small interference RNA (siRNA) in cisplatin-resistant ovarian cancer cells induced a significant cell growth arrest and inhibition of cell proliferation.

Apoptosis and arrest of cell cycle progression were also observed after siRNA-based silencing of c-MYC. Results were confirmed by Western blot analysis.

Nanoliposomal c-MYC-siRNA reduced the expression of c-MYC protein compared to the nanoliposomal C-siRNA group in mice bearing tumors.

Cisplatin treatment by itself did not induce a significant effect on tumor growth. On the other hand, decreased tumor weight was observed in the nanoliposomal c-MYC-siRNA group compared to the nanoliposomal C-siRNA group. This effect was further potentiated by cisplatin treatment (c-MYC-siRNA vs. c-MYC-siRNA+CIS).

Nanoliposomal c-MYC-siRNA induced a decrease in the number of tumor nodules compared to the nanoliposomal C-siRNA group. However, no further reduction in the number of tumor nodules was observed when cisplatin was combined with nanoliposomal c-MYC-siRNA.

These data advance c-MYC as a therapeutic target for cisplatin-resistant ovarian cancer.

Expression of c-MYC in Human Ovarian Cancer Patients and Ovarian Cancer Cells

To determine the clinical relevance of c-MYC in drug resistant ovarian cancer, the c-MYC mRNA levels were correlated with clinical data from ovarian cancer patients. Ovarian cancer patient data were downloaded and analyzed from "TCCA". Level 3 Illumina RNASeq "gene.quantification" files were used to extract MYC expression. Statistical analysis of c-MYC mRNA expression and clinical data from patients with high grade serous ovarian cancer showed that the PFS as shown in FIG. 11A through FIG. 11B and the OS as shown in FIG. 11C through FIG. 11D were significantly reduced for patients with higher c-MYC expression levels.

Figure 11A:
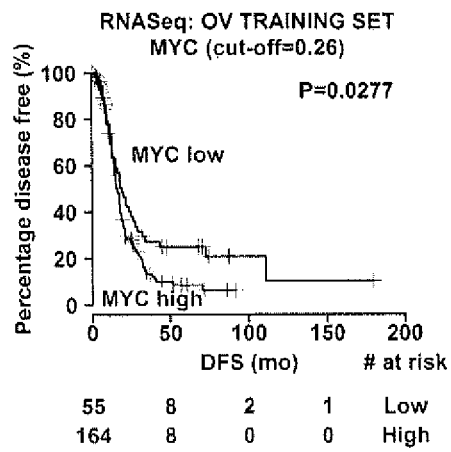
FIG. 11A-11D shows the c-MYC expression in ovarian cancer human tumors with data extracted from "the Cancer Genome Atlas" (TCGA) Data base.
Figure 11B:
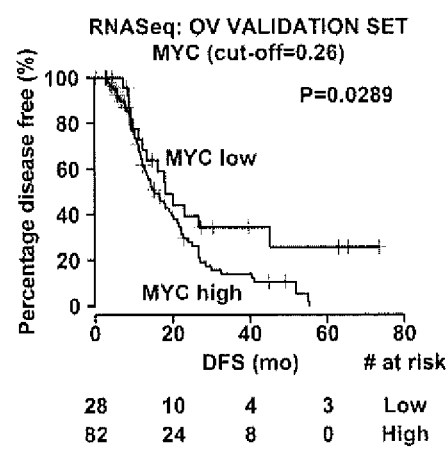
Figure 11C:
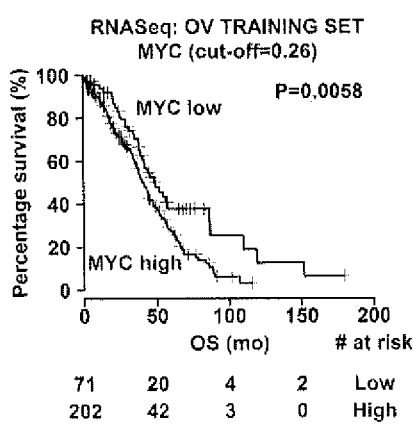
Figure 11D:
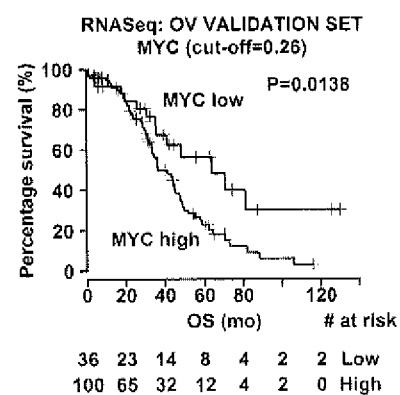

As shown in FIG. 11A through 11F, the entire cohort was separated into two sets, the training set (219 patients) shown in FIG. 11A and the validation set (110 patients) shown in FIG. 11B. The log-rank test revealed that the recurrence of the disease (expressed as percentage disease free) occurred significantly (P=0.0277) faster for patients with higher c-MYC expression levels as shown in FIG. 11A. This findings were corroborated with further analysis with the validation set cohort (P=0.0289) as shown in FIG. 11B. In addition, the overall survival (expressed as the percentage survival) was significantly reduced for patients with higher c-MYC expression values (P=0.0058) as shown in FIG. 11C. Statistical analysis with the validation set cohort corroborated these findings (P=0.0138).

To assess c-MYC protein levels, a panel of multiple ovarian cancer cell lines was evaluated by Western blot analysis. Interestingly, cisplatin-resistant cells (A2780CP20 and A2780CIS) expressed higher levels of c-MYC protein when compared to their sensitive counterparts (A2780) as shown in FIG. 8A-8B. The densitometric analysis of the band intensities confirmed these findings. The taxane-resistant ovarian cancer cells SKOV3.TR and HEYA8.MDR exhibited similar c-MYC levels when compared to their taxane-sensitive counterparts SKOV3ip1 and HEYA8, respectively. Together, these results show that c-MYC is a clinical relevant target for cisplatin resistant ovarian cancer patients.

Effects of c-MYC Silencing on Cell Growth, Proliferation, Apoptosis and Cell Cycle Progression.

FIG. 9A through 9C are directed to siRNA-based silencing of c-MYC. Two different siRNAs targeting exon 2 and exon 3 of the human c-MYC sequence (NM_002467) were used. FIG. 9A shows A2780CP20 cells ($2 \times 10^5$) transfected with 200 nM c-MYC-siRNA. Total protein was isolated from siRNA-transfected cells for Western blot analysis. Densitometric analysis of the intensities of the bands was calculated relative to the C-siRNA. Averages±SEM are shown (**P<0.0001). FIG. 9B shows A2780CP20 cells ($6 \times 10^4$) seeded into 6-well plates and 24-hr later 100 nM c-MYC-siRNA (2) or 100 nM C-siRNA was added to the cells. Eight hours post-transfection, 1000 cells were seeded into 10-cm Petri dishes. Seven days later, cells were stained and colonies of at least 50 cells were scored under a light microscope. The % of clonogenicity was calculated relative to C-siRNA. Averages±SEM are shown for three independent experiments (*P<0.001). FIG. 9C shows A2780CP20 cells ($2 \times 10^3$) seeded into 96-well plates and 24-hr later cells were transfected with a serial dilution of C-siRNA or c-MYC-targeted siRNAs. Cell viability was calculated 72-hr post-transfection. Percentages were obtained after blank OD subtraction, taking the untreated cells values as a normalization control. Averages±SEM are shown.

FIG. 10A-10C shows the effect of c-MYC-siRNA-mediated c-MYC silencing on cell cycle progression and apoptosis. A2780CP20 cells were transfected with 200 nM C-siRNA or c-MYC-targeted siRNA. The c-MYC siRNA activated apoptosis in almost 30% compared with the control siRNA. FIG. 10C is representative Western blots show changes in the levels of key proteins involved in apoptosis following c-MYC siRNA transfection.

Figure 19A:
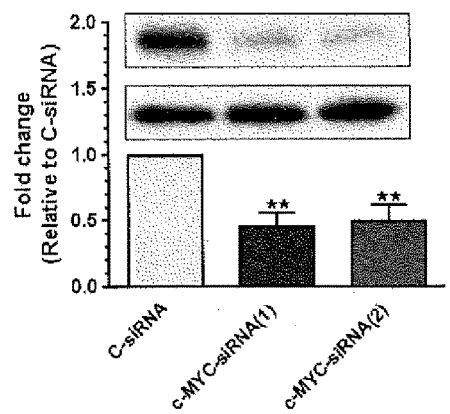
Figure 19B:
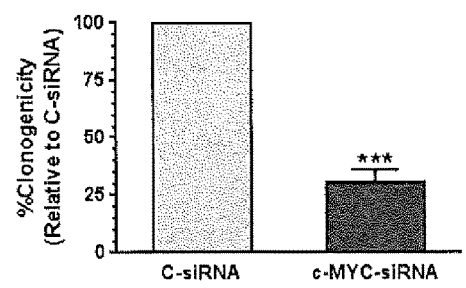
Figure 19C:
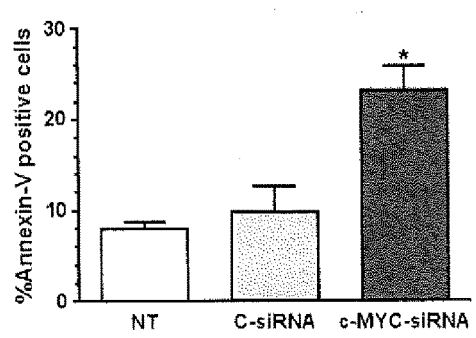
Figure 19D:
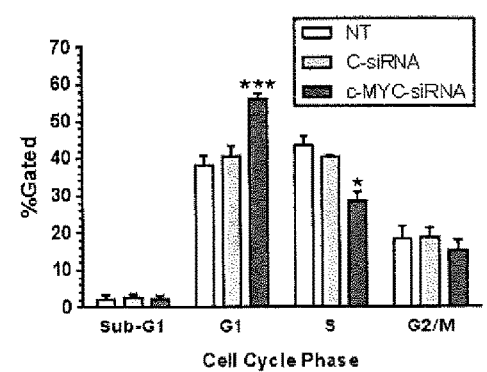
Figure 20A:
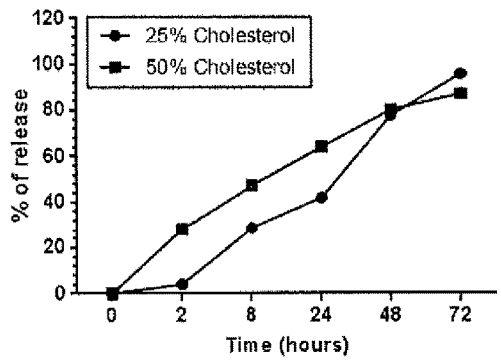
Figure 20B:
Figure 20C:
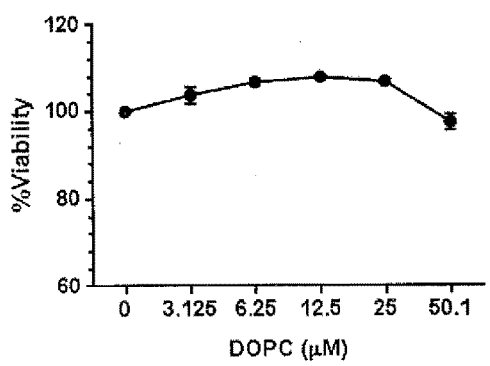
Figure 20D:
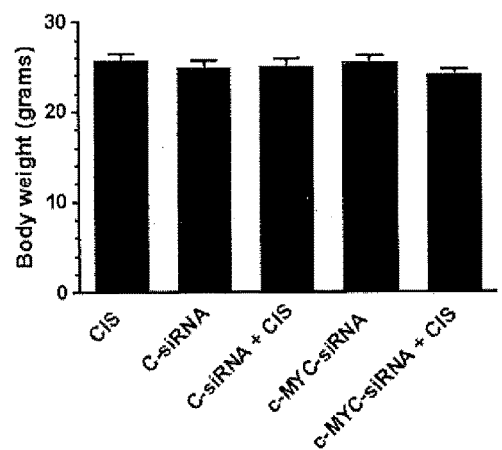

FIG. 12 shows A2780CIS cells ($9 \times 10^4$) seeded into 6-well plates and 24-hr later 100 nM c-MYC-siRNA (2) or 100 nM C-siRNA was added to the cells. Eight hours post-transfection, 2500 cells were seeded into 10-cm Petri dishes. Ten days later, cells were stained and colonies of at least 50 cells were scored under a light microscope. c-MYC siRNA reduced cell proliferation of A2780CIS cells in more than 50% compared with the control siRNA (****P<0.0001).

c-MYC siRNA did not induce cell toxicity in cells with low c-MYC expression levels (FIG. 13). In addition, the c-MYC-siRNA effect is potentiated by c-MYC (FIG. 14). C-MYC siRNA also had effects in proteins related with cell cycle progression (FIG. 15) AS shown in FIG. 8A through FIG. 15, it is clearly disclosed the biological effects of c-MYC silencing in cisplatin resistant ovarian cancer cells. Western blot analysis confirmed that the two siRNAs against c-MYC reduced dramatically the levels of c-MYC in the cisplatin-resistant ovarian cancer cell lines. Similar results were observed when c-MYC-siRNA was transfected into HEYA8 ovarian cancer cells (further see FIG. 19A-19D). Dose-dependent inhibition of cell growth was observed after 72-hr of c-MYC-targeted siRNAs treatment. The c-MYC siRNA growth inhibitory effects were observed even at doses as low as 12.5 nM of c-MYC-targeted siRNAs. Treatment with c-MYC-targeted siRNA also induced long-term in cell proliferation as evidenced in colony formation assays. Transient transfection of c-MYC-siRNA (2) in A2780CP20 cells reduced significantly (55%, p<0.001) the number of colonies formed after 7 days in culture compared with the c-siRNA-transfected cells. Similarly, transfection of c-MYC-siRNA (2) in A2780CIS and HEYA8 cells significantly reduced (48% and 70% reduction, P<0.0001 and *P<0.001, respectively) the number of colonies formed after 10 days in culture (FIG. 9B and FIG. 19B). On the other hand, silencing c-MYC in A2780 cisplatin-sensitive ovarian cancer cells, which express low c-MYC levels, induced negligible changes in cell proliferation (FIG. 13). Combination of a low-active c-MYC-siRNA (2) dose with a relatively low cisplatin dose (2 µM) induced significant (*P<0.05) additive-like effects in cell growth inhibition of A2780CP20 cells (FIG. 14) compared to c-MYC-siRNA (2) alone. These data suggest that c-MYC levels are associated with the sensitivity of ovarian cancer cells to cisplatin treatment.

Effect of c-MYC Overexpression in the Sensitivity of Ovarian Cancer Cells to Cisplatin Treatment As shown in FIG. 16A-16B the directed effect effects of c-MYC overexpression in ovarian cancer cells. A2780 cells ($9 \times 10^4$) were stably transfected with an empty vector (EV) or with a c-MYC-containing vector. FIG. 16A shows a Western blot analysis performed as previously described. Compared with untransfected cells or with empty vector clones, the c-MYC overexpressing clones showed higher c-MYC protein levels. FIG. 16B shows stable transfected A2780 cells exposed to CIS (1 µM final concentration)-containing RPMI-1640 media. Cell viability was calculated. Averages±SEM are shown relative to A2780-EV1 (*P<0.001, **P<0.0001) or to A2780-EV2 (###P<0.001, ####P<0.0001). FIGS. 18A, 18B and 18C are the effects of targeting c-MYC in ovarian mouse models with nanoliposomal formulations. liposomal-siRNAs were reconstituted in $Ca^{2+}$ and $Mg^{2+}$-free PBS. A Cryo-electron micrograph is shown in FIG. 17, discloses that the majority of the particles are small unilamellar vesicles in the 100-150 nm range. The hole in the image is a fenestration in the carbon support, which measures 1.2 microns in diameter. Nude mice were injected i.p. with A2780CP20 cells and randomly allocated in the groups FIG. 18A shows a Western blot analysis disclosing that c-MYC-siRNA-DOPC-PEG treatment reduced c-MYC protein levels in vivo. Therapy began one (1) week after tumor cell inoculation. FIG. 15B shows mean tumor weight and FIG. 15C shows the number of nodules recorded after 4-weeks. Averages±SEM are shown (*P<0.05, ****P<0.0001).

These data suggest that c-MYC contributes to the cisplatin resistant phenotype of ovarian cancer cells.

Characterization of Liposome-siRNA Formulations

Dynamic light scattering showed that the liposomes used in this study were slightly negative, and around 100-150 nm in diameter (See FIG. 5, FIG. 6 and FIG. 17). The percentage of cholesterol induced changes in the size but not in the surface charge (zeta potential) of the liposomal formulations (See FIG. 6). The efficiency of c-MYC-siRNA encapsulation was slightly higher for liposomes with 50% cholesterol (w/w DOPC) as compared with liposomes with 25% cholesterol (w/w DOPC) (See FIG. 6). A cryo-EM micrograph confirmed the particle size (100-150 nm) and showed that the majority of the liposomes are small unilamellar vesicles (see FIG. 17). The kinetics of c-MYC-siRNA release from liposomes with 25% cholesterol was slower in the first hours compared with liposomes with 50% cholesterol (see FIG. 20A). However, the kinetics of c-MYC-siRNA release was constant over time for liposomes with 50% cholesterol compared with 25% cholesterol. For these reasons, liposomes with 50% cholesterol were used for further studies. The ability of the liposomes to protect the stability of the c-MYC-siRNA from serum nucleases was evaluated in vitro. Results showed that c-MYC-siRNA degradation occurred faster for naked-siRNA compared to liposomal-siRNA (see FIG. 20B). Furthermore, the liposomal-c-MYC-siRNA formulation was not toxic in vitro even at DOPC concentrations as high as 50 µM. (see FIG. 20C). The size and charge of the reconstituted liposomal-c-MYC-siRNA formulations were stable over 2-hr at RT (See FIG. 22) and 4-weeks at 4° C. (FIG. 23). In vivo studies showed that a single injection of empty liposomes or liposomal-c-MYC-siRNA formulations did not induce early (5-hr) or late (24-hr) immune response (See FIG. 21A-21B). Repeated doses of liposomal-c-MYC-siRNA formulations (a single injection per day for 4 days, during 3 weeks) were not toxic for mice as indicated by the LDH activity or urea levels (see FIG. 21C-21D), which were similar to the control group (saline solution, only). No weight loss was noted during the treatment period (See FIG. 21E).

Therapeutic Effect of PEG-Liposomal c-MYC-siRNAs

DOPC-PEG-cholesterol-based nanoliposomes were used for in vivo c-MYC-siRNA delivery. First, we assessed whether the c-MYC silencing in vivo. Nude mice-bearing A2780CP20 tumors were injected i.p. with 5 µg of PEG-liposomal-c-siRNA or 5 µg of PEG-liposomal-c-MYC-siRNA. Seven days post-injection, mice were sacrificed and the tumors were dissected. c-MYC-siRNA-liposomal reduced the expression of total c-MYC at seven days post-injection (see FIG. 15D) compared with the control groups. The anti-tumor effects of c-MYC-siRNA as compared to c-siRNA were tested in A2780CP20 tumor-bearing mice. Tumor weight and number of nodules were assessed in five treatment groups (10 mice each): (a) C-siRNA, (b) cisplatin (CIS) alone, (c) c-MYC-siRNA, (d) C-siRNA plus CIS, and (e) c-MYC-siRNA plus CIS. All siRNA-DOPC (5 µg siRNA/injection) and CIS (160 µg/injection) treatments were injected i.p. once a week for 4 weeks. CIS treatment by itself did not induce a significant effect on tumor growth. On the other hand, decreased tumor weight was observed in the c-MYC-siRNA group (*p<0.05) compared with c-siRNA group of animals. This effect was further potentiated by CIS (c-MYC-siRNA vs. c-MYC-siRNA+CIS) (***P<0.001). c-MYC-siRNA induced a decrease in the number of tumor nodules (*p<0.05) compared with c-siRNA group (see FIG. 15F).

In the present disclosure, it was shown that high levels of c-MYC are associated with faster recurrence and poor overall survival of patients with high grade serous ovarian cancer, and with cisplatin resistance in ovarian cancer cells. Another object of the present disclosure was to provide that c-MYC-siRNA-based silencing of c-MYC inhibits cell proliferation in vitro and reduces tumor growth in xenograft models of cisplatin-resistant ovarian cancer. c-MYC, an oncoprotein highly abundant in several types of cancer, is considered an undruggable molecule by virtue of its flat protein surface. Thus, the evidence we present here shows that siRNA-based c-MYC targeting is a therapeutic modality for ovarian cancer patients expressing high c-MYC levels, including those that are resistant to cisplatin treatment. The c-MYC transcription factor, which regulates approximately 15% of all human genes, plays an important role in a myriad of biological processes including cell growth and proliferation, cell cycle progression, apoptosis, angiogenesis, senescence and genomic instability. In addition, c-MYC regulates the expression of not only a particular group of genes but acts in concert with RNA polymerase and transcription factors as a universal amplifier of gene expression in embryonic stem cells and tumor cells. In fact, c-MYC amplification has been reported in multiple malignancies including ovarian cancer. In other tumor types, c-MYC expression levels have been associated with drug resistance. For instance, Sakamuro and co-workers have shown that c-MYC oncoprotein increases cisplatin resistance by decreasing production of the c-MYC inhibitor bridging integrator 1

(BIN1). The present disclosure relates to the role of ectopic expression of c-MYC in decreasing the sensitivity of ovarian cancer cells to cisplatin treatment.

Current adjuvant chemotherapy for ovarian cancer includes cisplatin and paclitaxel; unfortunately, the majority of the patients develop chemoresistance which leads to therapeutic failure. Thus, the present disclosure provides further evidence that c-MYC is a plausible target for ovarian cancer patients with high c-MYC expression levels. Moreover, the findings that the c-MYC-targeted siRNA did not affect the viability of cells with low c-MYC protein levels, suggests that c-MYC could be considered as a potential biomarker and an indicative of chemotherapy response.

We have shown that c-MYC siRNA-based silencing induces short- and long-term effects in cell growth and proliferation. These effects were associated with both apoptosis induction, and cell cycle arrest. Future studies should determine the c-MYC-regulated anti-apoptotic genes associated with the cisplatin resistance in ovarian cancer cells. Further one of the major cell cycle inhibitory proteins, p27, was increased following c-MYC depletion. Similarly, decreased levels of CDK4 and cyclin D3 following c-MYC silencing occurred by the ability of c-MYC to transcriptionally regulate the expression of these proteins.

In conclusion, the present formulation and method for DOPC-PEG-liposomal c-MYC-targeted siRNA alone or in combination with chemotherapy is efficacious against ovarian cancer.

The invention is not limited to the precise configuration described above. While the invention has been described as having a preferred design, it is understood that many changes, modifications, variations and other uses and applications of the subject invention will, however, become apparent to those skilled in the art without materially departing from the novel teachings and advantages of this invention after considering this specification together with the accompanying drawings. Accordingly, all such changes, modifications, variations and other uses and applications which do not depart from the spirit and scope of the invention are deemed to be covered by this invention as defined in the following claims and their legal equivalents. In the claims, means-plus-function clauses, if any, are intended to cover the structures described herein as performing the recited function and not only structural equivalents but also equivalent structures.

All of the patents, patent applications, and publications recited herein, and in the Declaration attached hereto, if any, are hereby incorporated by reference as if set forth in their entirety herein. All, or substantially all, the components disclosed in such patents may be used in the embodiments of the present invention, as well as equivalents thereof. The details in the patents, patent applications, and publications incorporated by reference herein may be considered to be incorporable at applicant's option, into the claims during prosecution as further limitations in the claims to patently distinguish any amended claims from any applied prior art.

What is claimed is:

1. A compound for treating cancer cells in a mammal, wherein said compound is a nanoliposomal formulation comprising a ratio of 1 μg c-MYC-siRNA, 10 μg 1,2-Dioleoyl-sn-glycero-3-phosphocholine (DOPC), cholesterol in the range between 25% to 50% (w/w) of DOPC and 10% DSPE-PEG-2000 (mol/mol) of DOPC, wherein the nanoliposomal formulation has a mean particle size in the range of 93 to 116.2 nanometers; and wherein the nanoliposomal formulation has a mean Z potential in the range of −2.50 to −2.81 millivolts.

2. The compound of claim 1, wherein the selected concentration for said nanoliposomal formulation comprises cholesterol 40% (w/w) of DOPC.

* * * * *